United States Patent [19]

Zhao et al.

[11] Patent Number: 5,814,488

[45] Date of Patent: Sep. 29, 1998

[54] SEMISYNTHETIC 1-N-ETHYLGENTAMICIN $C_{1A}$ AND METHOD FOR ITS PREPARATION

[75] Inventors: Min Zhao; Jin Fan; Jun Liu; Xiaoling Hu; Minqi Fan, all of Wuxi, China

[73] Assignee: Jiansgu Institute of Microbiology, Wuxi, China

[21] Appl. No.: 537,784

[22] PCT Filed: Apr. 23, 1994

[86] PCT No.: PCT/CN94/00029

§ 371 Date: Jan. 5, 1996

§ 102(e) Date: Jan. 5, 1996

[87] PCT Pub. No.: WO94/25566

PCT Pub. Date: Nov. 10, 1994

[30] Foreign Application Priority Data

Apr. 23, 1993 [CN] China ................................ 93112412.3

[51] Int. Cl.⁶ .................................................... C12N 1/20
[52] U.S. Cl. .................... 435/84; 435/252.1; 435/172.1; 435/172.2; 536/13.6
[58] Field of Search ............................. 435/252.1, 172.1, 435/172.2, 84; 536/13.6

[56] References Cited

U.S. PATENT DOCUMENTS

| | | | |
|---|---|---|---|
| 3,091,572 | 5/1963 | Luedeman | 435/84 |
| 4,029,882 | 6/1977 | Wright | 536/17 |
| 4,044,123 | 8/1977 | Daniels et al. | 424/180 |
| 4,063,015 | 12/1977 | Mallams | 536/17 |
| 4,230,847 | 10/1980 | Nagabhushan et al. | 536/10 |
| 4,387,219 | 6/1983 | Yamamoto et al. | 536/13.6 |
| 4,412,068 | 10/1983 | Rosi | 536/13.6 |

FOREIGN PATENT DOCUMENTS 86 1 08119  6/1988  China .

OTHER PUBLICATIONS

Y. Yun–liu et al., "Comparison of antibacterial activities of three C components of Gentamicin against *p. aeruginosa* strains", *Antibiotics* 7(1): 12–15 (1982).

Zhao et al., Kangshengsu (1984), 9(2), 94–8 (I).

Zhao et al., Zhongguo Kangshengsu Zazhi (1992), 17(1), 16–20 (II).

Wright et al., J. Chem Soc. Chem. Commun, (6). 206–208, 1976.

The Merck Index, Tenth Edition, p. 627.

*Primary Examiner*—Irene Marx
*Attorney, Agent, or Firm*—Foley & Lardner

[57] ABSTRACT

This invention relates to the fields of microbiology and antibiotics. Particularly, it relates to a new mutant strain, a method of its mutation breeding, to a monocomponent Gentamicin $C_{1a}$ produced by this strain which is used as mother nucleus of semisynthetic antibiotic 1-N-ethylgentamicin $C_{1a}$, and to compositions composed of semisynthetic 1-N-ethylgentamicin derivatives as active component and pharmaceutically acceptable accitives and their manufacturing methods.

17 Claims, 9 Drawing Sheets

1. GM ($C_{1a}$, $C_2$, $C_1$)
2. $GMC_{1a}$
3. PRODUCT OBTAINED BY FERMENTATION OF CGMCC 0197. ($GMC_{1a}$)
4. $GMC_{2b}$

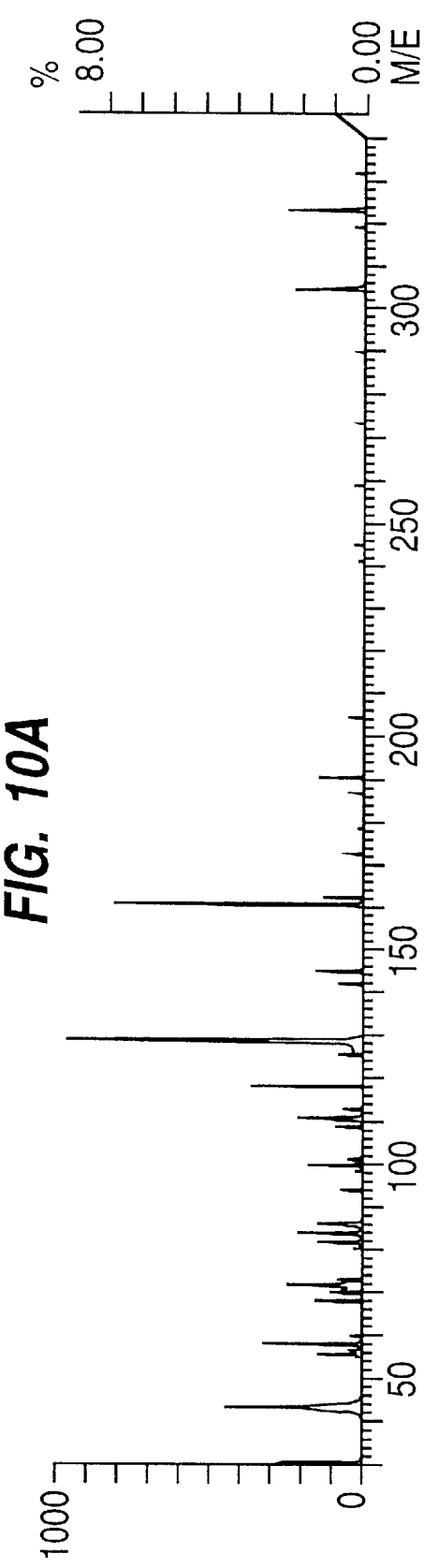
FIG. 10A
FIG. 10B

SEMISYNTHETIC 1-N-ETHYLGENTAMICIN $C_{1A}$ AND METHOD FOR ITS PREPARATION

FIELD OF THE INVENTION

This invention relates to the fields of microbiology and antibiotics. Particularly, it relates to a new mutant strain, a method of its mutation breeding, to a monocomponent Gentamicin $C_{1a}$ produced by this strain and used as mother nucleus of semisynthetic antibiotic 1-N-ethylgentamicin $C_{1a}$ (1-N-Ethylgentamicin $C_{1a}$ being named Etimicin) to compositions composed of semisynthetic 1-N-ethylgentamicin derivatives as active component and pharmaceutically acceptable additives and their manufacturing methods.

BACKGROUND OF THE INVENTION

It is well known that there are three main components in Gentamicin (GM) which is produced by fermentation of present strains: Gentamicin $C_1$ ($GMC_1$), Gentamicin $C_2$ ($GMC_2$) and Gentamicin $C_{1a}$ ($GMC_{1a}$). The quality as well as the effect of Gentamicin have direct relationship with the content of the three components. In ((Antibiotics)) Vol.7 No. 1 12~15, 1982, Mr. Yang Yun-liu et al. from the Academy of Sciences of China reported the Minimal Inhibitory Concentrations (MIC) against 74 strains of *P.aeruginosa* separated clinically and the values of $LD_{50}$ to each component of gentamicin C. The component $GMC_{1a}$ was considered best. If a monocomponent gentamicin is to be separated and purified from multi-component gentamicin, complicated technology and equipments are required and the production cost is thus raised. In order to overcome these shortcomings, strains which produce a monocomponent gentamicin are needed. Gentamicin as a kind of aminoglycoside antibiotics was first found in 1963 by M. J. Weisten et al. of Schering Corporation of America, and it has been about twenty years since 1963 when it appeared on the market. Nowadays, gentamicin is still widely used clinically. But, because of its side-effects of ototoxicity and nephrotoxicity, the use of gentamicin is to some extent restricted in medical treatment. It is desired to develop a kind of novel gentamicin derivative that is of low toxicity and high efficiency, especially active against gentamicin-resistant strains.

In the research references, U.S. Pat. No. 4,230,847 discloses a compound of aminoglycoside antibiotics, a gentamicin derivative in which some amino groups of gentamicin are selectively protected. U.S. Pat. Nos. 4,063,015 and 4,044,123 disclose 1,3,2'-tri-N-acetylgentamicin which is an antibiotic and useful as an intermediate in the preparation of 6'-N-alkylaminoglycoside. Canadian Patent 1,034,573 discloses a method for preparing 1-N-replaced-4,6-diaminoglycosyl-1,3-diaminocyclitols. In the prior art, no one has found a strain which produces monocomponent gentamicin, and there is no report about the semisynthesic 1-N-ethylgentamicin derivatives and their compositions in which monocomponent gentamicin produced by fermentation of the strain is used as intermediate (mother nucleus).

DISCLOSURE OF THE INVENTION

The first object of this invention is to provide a strain by which monocomponent gentamicin can be produced. The said strain was deposited in the Centre of General Microorganisms Collection of China (abbreviated to CGMCC, address: Institute of Microbiology, Academia Sinica, Zhongguancun, Beijing 100090, P.R.China) on Apr. 23, 1993, and was accepted for deposit under the Budapest Treaty on the International Recognition of the Deposit of Microorganism for the purpose of Patent Procedure on Nov. 27, 1995. The strain is a *M. echinospora* mutant and its registration number is CGMCC0197.

The second object of this invention is to provide a method of mutation breeding by means of which the above strain can be obtained. The monospore suspension of *Micromonospora echinospora*, after exposure to UV for 3 min and 0.5% LiCl solution treatment for 30 min, is spread on a plate containing Micronomicin (2000 ug/ml), and cultured for 14 days at 37° C. The monocolony is picked up and screened to obtain *Micromonospora echinospora* mutant CGMCC0197.

The third object of this invention is to provide a process for the preparation of 1-N-ethylgentamicin C derivatives of general formula [1]

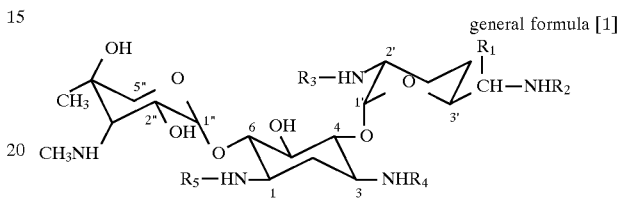

general formula [1]

Wherein:

|  | $R_1$ | $R_2$ | $R_3$ | $R_4$ | $R_5$ |
|---|---|---|---|---|---|
| (1) 1-N-ethylgentamicin $C_1$ | $CH_3$ | $CH_3$ | H | H | $C_2H_5$ |
| (2) 1-N-ethylgentamicin $C_2$ | $CH_3$ | H | H | H | $C_2H_5$ |
| (3) 1-N-ethylgentamicin $C_{1a}$ | H | H | H | H | $C_2H_5$ |
| (4) 1-N-ethylgentamicin $C_{2b}$ | H | $CH_3$ | H | H | $C_2H_5$ |
| or their acid addition salts |  |  |  |  |  |

The process consists of:

(1) gentamicin $C_1$, or gentamicin $C_2$, gentamicin $C_{1a}$ and gentamicin $C_{2b}$ used as mother nucleus is dissolved in an aprotic solvent, followed by the protection of amino groups except amino group at position 1 with acyl group in the presence of divalent transition metal salt;

(2) the amino group at position 1 is ethylated with acetaldehyde in the presence of a reductant;

(3) all protecting groups are removed by hydrolysis;

(4) 1-N-ethylgentamicin C derivative is isolated in free base form or in the form of an acid addition salt.

The process is characterized in that gentamicin $C_{1a}$ used for the synthesis of 1-N-ethylgentamicin $C_{1a}$ is obtained from fermentation broth of *Micromonospora echinospora* mutant CGMCC-0197 with an ion-exchange extraction procedure and further characterized in that the preparation process of gentamicin $C_{1a}$ includes the following steps:

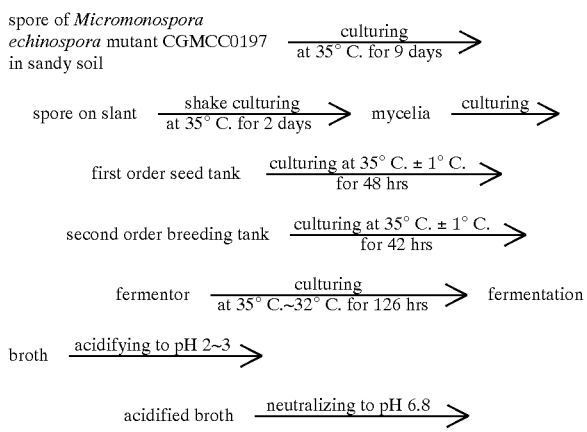

-continued

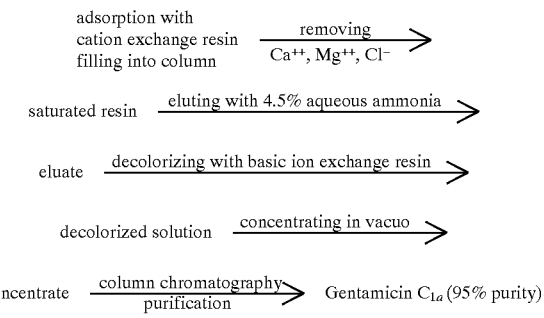

A object of this invention is to provide a semisynthetic antibiotic of 1-N-ethylgentamicin derivative of general formula [1] or its salts.

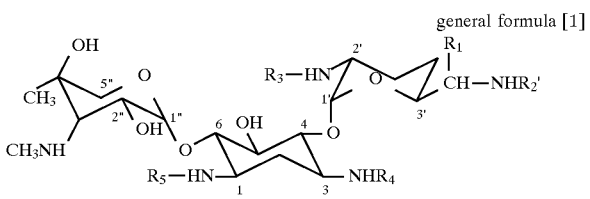

general formula [1]

characterized by $R_5$ being ethyl group, $R_1$ and $R_2$ independently being methyl group or hydrogen;

and further characterized in that $R_5$ is ethyl group, $R_1$ being hydrogen, and $R_2$ being methyl group or hydrogen independently;

or further characterized in that $R_1$ as well as $R_2$ are hydrogen and $R_5$ is ethyl group.

another object of this invention is to provide a composition consisting of 0.01 to 99.99% (by weight) 1-N-ethylgentamicin C derivative or its salts (as an active component) of general formula [1]:

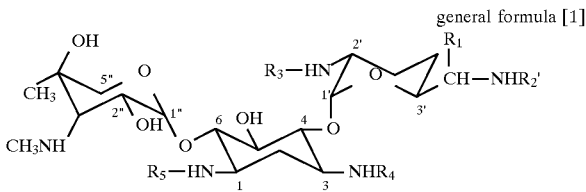

general formula [1]

|  | $R_1$ | $R_2$ | $R_3$ | $R_4$ | $R_5$ |
|---|---|---|---|---|---|
| (1) 1-N-ethylgentamicin $C_1$ | $CH_3$ | $CH_3$ | H | H | $C_2H_5$ |
| (2) 1-N-ethylgentamicin $C_2$ | $CH_3$ | H | H | H | $C_2H_5$ |
| (3) 1-N-ethylgentamicin $C_{1a}$ | H | H | H | H | $C_2H_5$ |
| (4) 1-N-ethylgentamicin $C_{2b}$ | H | $CH_3$ | H | H | $C_2H_5$ | and 99.99 to 0.01% (by weight) pharmaceutically acceptable carrier.

The composition is further characterized in that in the formula of the active component, $R_5$ is ethyl group, $R_1$ is hydrogen and $R_2$ is methyl group or hydrogen, or characterized in that in the formula of active component, $R_5$ is ethyl group, and $R_1$ as well as $R_2$ are hydrogen.

The following appending figures and examples further illustrate the present invention. IR means infrared ray. UV means ultraviolet ray. NMR means nuclear magnetic resonance. MS means mass spectrometry. TLC means thin layer chromatography.

BRIEF DESCRIPTION OF THE DRAWINGS

FIG. 10. MS spectrum of the product obtained by fermentation of *M.echinospora* mutant CGMCC0197.

THE BEST MODE FOR CARRYING OUT THE INVENTION

The Preparation of 1-N-Ethylgentamicin $C_{1a}$

Figure 1:
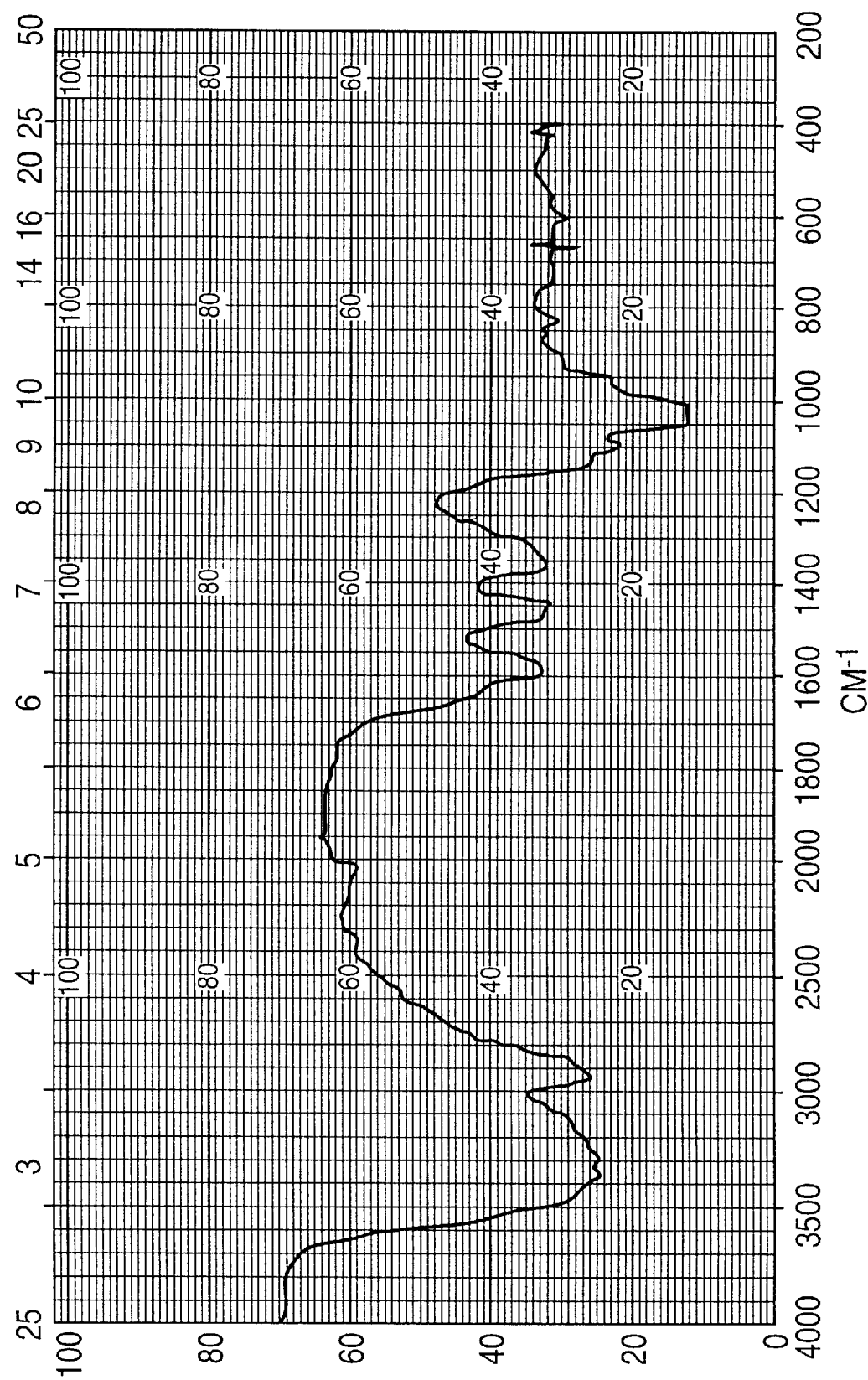
FIG. 1. IR spectrum of 1-N-ethylgentamicin $C_{1a}$.

1. The preparation of *Micromonospora echinospora* mutant by induced mutation

The original strain of *Micromonospora echinospora* was exposed to UV for 3 min, and then treated with 0.5% LiCl for 30 min. After this, the monospore suspension was spread on a plate containing 2000 ug/ml Micronomicin, and was cultured at 37° C. for 14 days. The monocolony was picked up and screened to obtain *Micromonospora echinospora* mutant CGMCC0197, which was then slant cultured and sand tube preserved.

2. The preparation of mother nucleus Gentamicin $C_{1a}$ (GMC$_{1a}$)

Fermentation of *M.echinospora* mutant CGMCC0197 producing monocomponent GMC$_{1a}$ is a three steps process. Gentamicin $C_{1a}$ was extracted from the broth (800 unit/ml, content>85%) with ion-exchange resin and then was refined to obtain gentamicin $C_{1a}$ (purity 90–95%).

The procedure is shown in the following:

```
spore of Micromonospora
echinospora mutant CGMCC0197  --culturing at 35° C. for 9 days-->
in sandy soil spore on slant  --shake culturing at 35° C. for 2 days-->  mycelia  --culturing--> first order seed tank  --culturing at 35° C. ± 1° C. for 48 hrs--> second order breeding tank  --culturing at 35° C. ± 1° C. for 42 hrs--> fermentor  --culturing at 35° C.~32° C. for 126 hrs-->  fermentation broth  --acidifying to pH 2~3--> acidified broth  --neutralizing to pH 6.8--> adsorption with
cation exchange resin  --removing Ca++, Mg++, Cl- -->
filling into column saturated resin  --eluting with 4.5% aqueous ammonia--> eluate  --decolorizing with basic ion exchange resin--> decolorized solution  --concentrating in vacuo-->
```

-continued

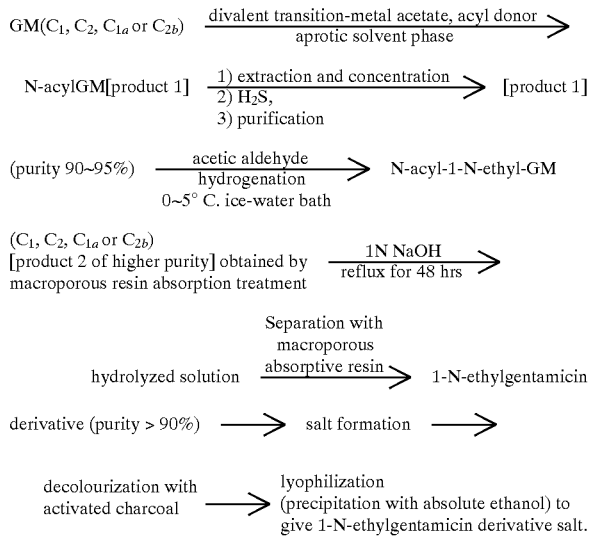

3. Synthesis of 1-N-ethylgentamicin derivatives

Example 1 Method of Obtaining CGMCC0197 by Induced Mutation Breeding 10 ml sterilized water was added to one slant of M.echinospora JIM-401, and spores were scraped down and removed into a sterilized shake flask filled with glass balls. The flask was shaken for 15 min. The spore solution was filtered through sterilized filter paper to obtain monospora suspension. The suspension was diluted and treated with 0.3% LiCl at 30° C. for 30 min, then with UV (30 W) for 3 min. The treated suspension was diluted with sterilized water, spread on dishes containing 2000 ug/ml Micronomicin, and cultured at 35° C. for 14 days. Monocolonys were picked up and seeded on the slant, and were cultured at 37° C. for 8 days, then it was seeded in a shake flask, and shake-cultured at 35° C. for 6 days. The broth was detected with TLC and M.echinospora mutant CGMCC0197 was obtained. The mutant differed from original strain in cultural characteristics, physiologico-biochemical properties, carbon source utilization and products of fermentation. The mother strain produces Micronomicin (60%~70%) as the main component and gentamicin $C_{1a}$ (20%), but the mutant CGMCC0197 only produces a monocomponent antibiotic, which is the same as gentamicin $C_{1a}$ ($GMC_1$) identified by means of TLC, UV, IR, NMR, MS.

The comparisons of cultural characteristics, physiologico-biochemical properties and carbon source utilization between JIM-202 (CGMCC0197) and JIM-401 are shown in tab.1~3 respectively.

Amino acid analysis of hydrolyzate of whole cell of CGMCC0197 shows that CGMCC0197 contains glycine and meso-diaminopimelic acid.

The TLC, UV, IR, NMR, MS of the product produced by the mutant CGMCC0197 are shown in FIG. 7–10 respectively.

Example 2 Preparation of Gentamicin $C_{1a}$

The spore suspension of CGMCC0197 strain was inoculated in 100 L breed medium. After being cultured for 48 hrs at 35° C.±0.5° C. with aeration (1.2 $V \cdot V^{-1} min^{-1}$) and stirring (230 rpm), it was inoculated in 2000 L medium for generation under the above culture condition. 24 hrs later, it was inoculated in 6500 L fermentation medium with an initial aerating at $0.5V \cdot V^{-1} min^{-1}$ for 6 hrs, then cultured for 126 hrs under the condition of aerating (1.0 $V \cdot V^{-1} min^{-1}$) and stirring (180 rpm) at 34° C.±0.5° C. 1500 L medium was added respectively after 24 hr and 60 hr, and 1000 L water added after 84 hr. Thus, 9000 L $GMC_{1a}$ fermented broth was obtained (biochemical measure potency 880 ug/ml). The broth was adjusted to PH 2.5 with concentrated hydrochloric acid, heated to 70° C. and maintained for 10 min, then the pH of the broth was brought to 6.8 by the addition of 6 $mol \cdot L^{-1} NaOH$, 120 L 732($NH_4^+$) ion exchange resin was added to it and the resulting mixture was stirred for 5 hrs. The resin was filled into a column and washed with water. The resin was eluted with 2 $mol \cdot L^{-1}$ $NH_3 \cdot H_2O$. The eluate was decolourized via a column of C290 ($OH^-$) resin and concentrated in vacuo to 80 L, then absorbed by 450 L YPR-II resin column (40×400 cm), and was eluted with 20% ethanol aqueous solution after being washed with water. The eluates containing $GMC_{1a}$ were pooled and concentrated in vacuo to 50 L and lyophilized to give 6050 g $GMC_{1a}$ with a purity of 90~95%.

732($NH_4^+$) and C290 ($OH^-$) resins were made in Shanghai Resin Factory, China.

YPR-II resin was made in Yangzhou Pharmaceutical Factory, China.

Example 3 Preparation of Gentamicin $C_{1a}$ Sulfate

The spore suspension CGMCC0197 was inoculated to 500 ml seed flask containing 100 ml of seed medium, cultured with shaking (220 rpm) at 35° C.±0.50° C. for 40 hours. Then the seeds of five flasks were inoculated into a fermentor containing 10 L fermentation medium, cultured at 35° C.±0.5° C. for 120 hrs with aerating (1 $V \cdot V^{-1} min^{-1}$) and stirring, meantime, sterilized water was supplemented for the vapourized water. The fermented broth (9.5 L) (820 ug/ml) obtained was brought to pH 3 by the addition of oxalic acid, heated to 70° C. and maintained for 10 min, then adjusted to pH 6.8 by the addition of 6 $mol \cdot l^{-1}$ NaOH. After filtration, the antibiotics was extracted on a column of 120 ml 732($NH_4^+$) resin from the filtrate. After washing with water, the column was eluted by 2 $mol \cdot L^{-1} NH_3 \cdot H_2O$, and the eluant was decolourized by 120 ml 711($OH^-$) resin and was concentrated to 60 ml in vacuo, the solution was brought to pH 5 by the addition of 3 $mol \cdot L^{-1}$ $H_2SO_4$. After the addition of 5 g activated charcoal, it was maintained at 60° C. for 30 min, and filtered to remove the activated charcoal. The filtrate was lyophilized to give 9 g $GMC_{1a}$ sulfate (90~95% purity).

Example 4 Preparation of 1-N-ethylgentamicin $C_{1a}$ (1) 3,2',6'-tri-N-acetylgentamicin $C_{1a}$ Gentamicin $C_{1a}$ (10 g,22 mmol) was dissolved in dimethylsulfoxide (400 ml), and Cobalt(II) acetate tetrahydrate (11 g,44 mmol) was added with stirring at 25° C. After 20 min of reaction at 25° C., a freshly prepared 1M solution of acetic anhydride in tetrahydrofuran (56 ml) was added dropwise. Then the reaction mixture was stirred for a further period of 1 h, diluted with water (500 ml) and adjusted to pH 4 with 2 $mol \cdot L^{-1}$ hydrochloric acid. The product was absorbed on a column of 732($NH_4^+$, 4×30 cm) resin, washed with water (2000 ml) and eluted with 2 $mol \cdot L^{-1}$ ammoniun hydroxide. The eluates containing the product were pooled and concentrated in vacuo to 100 ml. Hydrogen sulfide was bubbled through the concentrate until all cobalt was completely precipitated. The solids were removed by filtration through diatomite. The filtrate was concentrated to 50 ml and lyophilized to give 3,2',6'tri-N-acetyl-gentamicin $C_{1a}$ (12.2 g, 85% purity, 80% yield).

(2) 1-N-ethyl-3,2',6'-tri-N-acetylgentamicin $C_{1a}$

The pH of a stirred and cooled (3° C.) solution of 3,2',6'-tri-N-acetylgentamicin $C_{1a}$ (10 g) in water (200 ml)

was brought to 2.5 by the addition of 1M hydrochloric acid. A freshly prepared solution of 40% aqueous acetaldehyde-tetrahydrofuran (1:1, 10 ml) was added with stirring. The pH of the mixture was brought to 4 by the addition of 2.5% aqueous sodium borohydride solution dropwise at 3° C. After 1 hour of reaction, the process above was repeated until the 3,2',6'-tri-N-acetyl-gentamicin $C_{1a}$ spot was not observed on TLC in the lower phase of a chloroform-methane-28% aqueous ammonia (2:1:1). The mixture was concentrated in vacuo to remove acetaldehyde and the residue chromatographed on a column (4.0×50 cm) of YPR-II resin with the solutions of 5%, 10%, 20% ethanol containing 0.5M ammonium hydroxide as the eluant. The eluates containing the product were pooled, concentrated and lyophilized to give 1-N-ethyl-3,2',6'-tri-N-acetylgentamicin $C_{1a}$ (5.6 g, 62% yield).

(3) 1-N-ethylgentamicin $C_{1a}$ 5.0 g of 1-N-ethyl-3,2',6'-tri-N-acetylgentamicin $C_{1a}$ was dissolved in 100 ml of 1M sodium hydroxide and heated under reflux (100° C.) for 48 hours. After cooling, the solution was diluted to a volume of 1000 ml and the solution was stirred with 732 ion-exchange resin ($H^+$, 100 ml) until the pH of the solution was brought to 9. The resin was removed by filtration, washed with water and filled into a column, eluted with 2 mol·L$^{-1}$ ammonium hydroxide. The eluate was evaporated in vacuo and the residue was chromatographed on a column (2.5×30 cm) of YPR-II resin with the solutions of 5%, 7.5%, 15% ethanol containing 0.5M ammonium hydroxide as the eluant. The eluates containing 1-N-ethyl-gentamicin $C_{1a}$ were pooled, evaporated in vacuo, and lyophilized to give a pure product (2.7 g, 70% yield).

(4) 1-N-ethylgentamicin $C_{1a}$ Sulphate

Pure 1-N-ethylgentamicin $C_{1a}$ (2 g) was dissolved in water (15 ml), the pH being brought to 5.8 by the addition of 3M $H_2SO_4$ (3.5 ml). Activated charcoal (1 g) was added. The suspension was stirred for 30 min at 60° C., followed by filtration. The filtrate was lyopillized to give 1-N-ethylgentamicin $C_{1a}$ sulphate (2.2 g, 91% yield).

The structure of the last product in example 4 was determinated by means of instrumental analysis as follows:

1. IR spectrum as shown in FIG. 1 was obtained by the use of 399-B Infrared spectrophotometer (VS. PECO). It is a typical IR spectrum of aminoglycoside.

Figure 2:
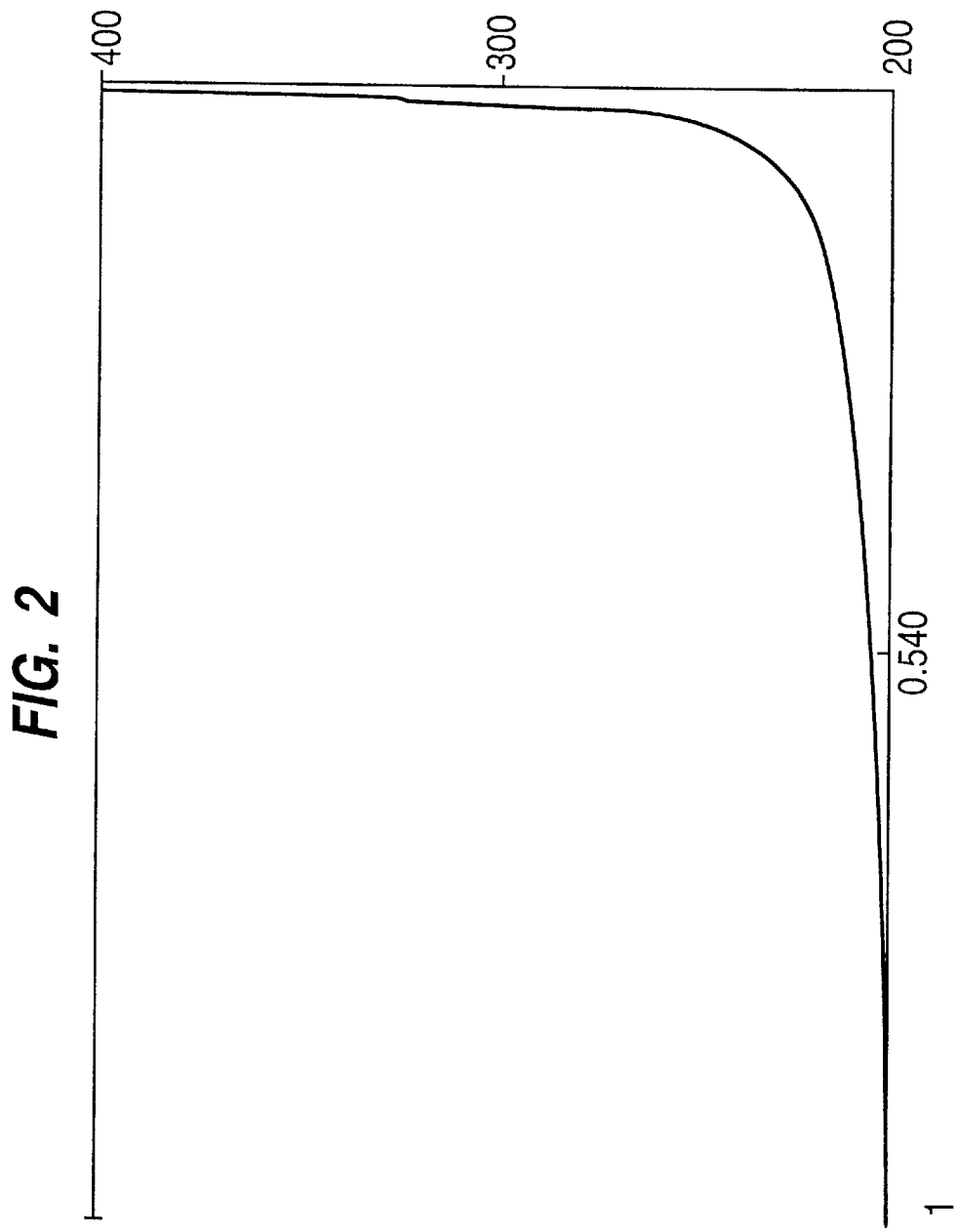
FIG. 2. UV spectrum of 1-N-ethylgentamicin $C_{1a}$.

2. UV absorption spectrum as shown in FIG. 2 was obtained by the use of a UV-240 spectrophotometer (SHMADUZ), $H_2O$ as solvent. It is characterized by no absorption at 200 nm to 400 nm.

Figure 3:
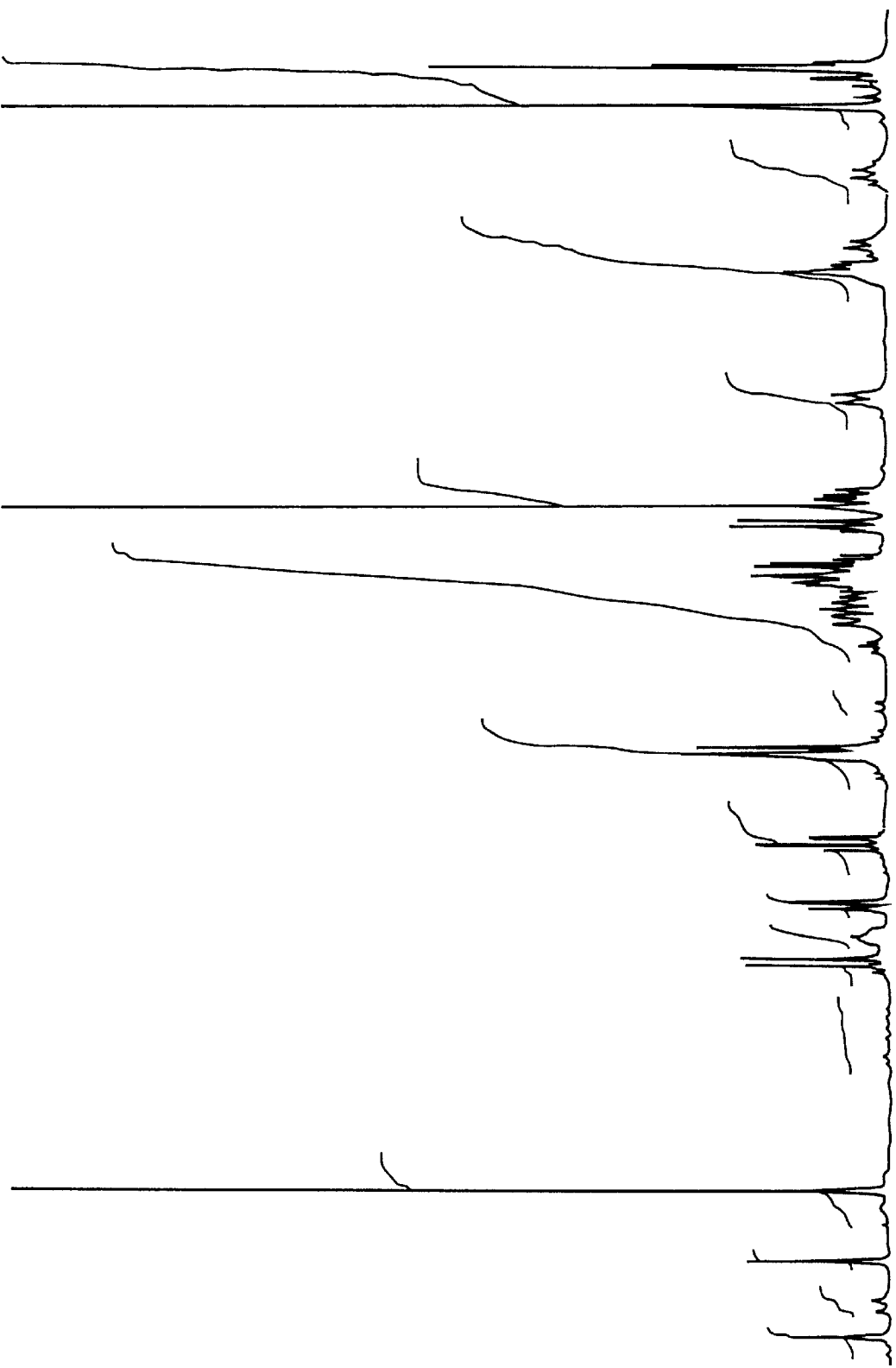
FIG. 3. $^1$H-NMR spectrum of 1-N-ethylgentamicin $C_{1a}$.

3. $^1$H-NMR spectrum as shown in FIG. 3 was obtained by the use of AM500NMR spectrometer (BRUKER.CO), deuterium oxide as solvent, tetramethylsilane (TMS) as internal standard, resonance frequency making 500.13 MHz.

Figure 4:
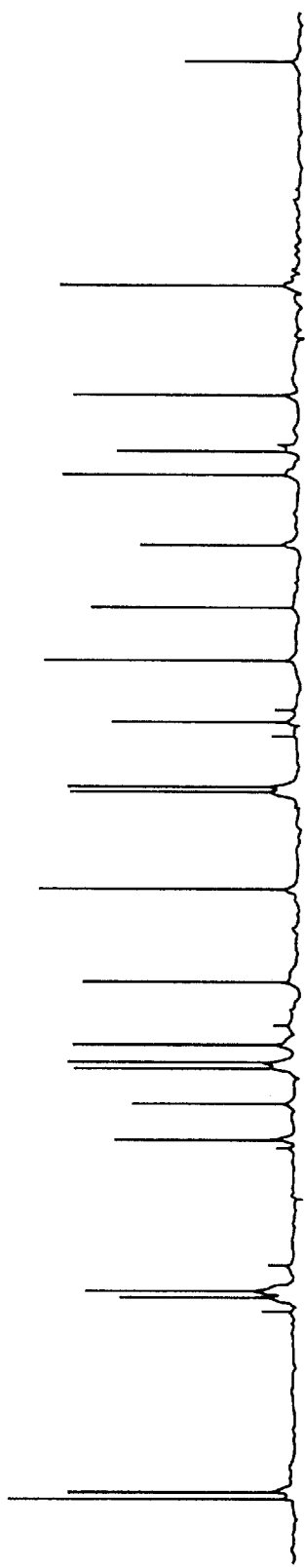
FIG. 4. $^{13}$C-NMR spectrum of 1-N-ethylgentamicin $C_{1a}$.

4. $^{13}$C-NMR spectrum as shown in FIG. 4 was obtained by the use of AM-500 NMR spectrometer, deuterium oxide as solvent, tetramethylsilane (TMS) as internal standard, resonance frequency making 125.76 MHz. The characteristic peak of 47.02 ppm corresponds to the carbon of methylene of 1-N-ethyl group. The peak of 16.43 ppm corresponds to the carbon of methyl group of 1-N-ethyl group.

Figure 5A:
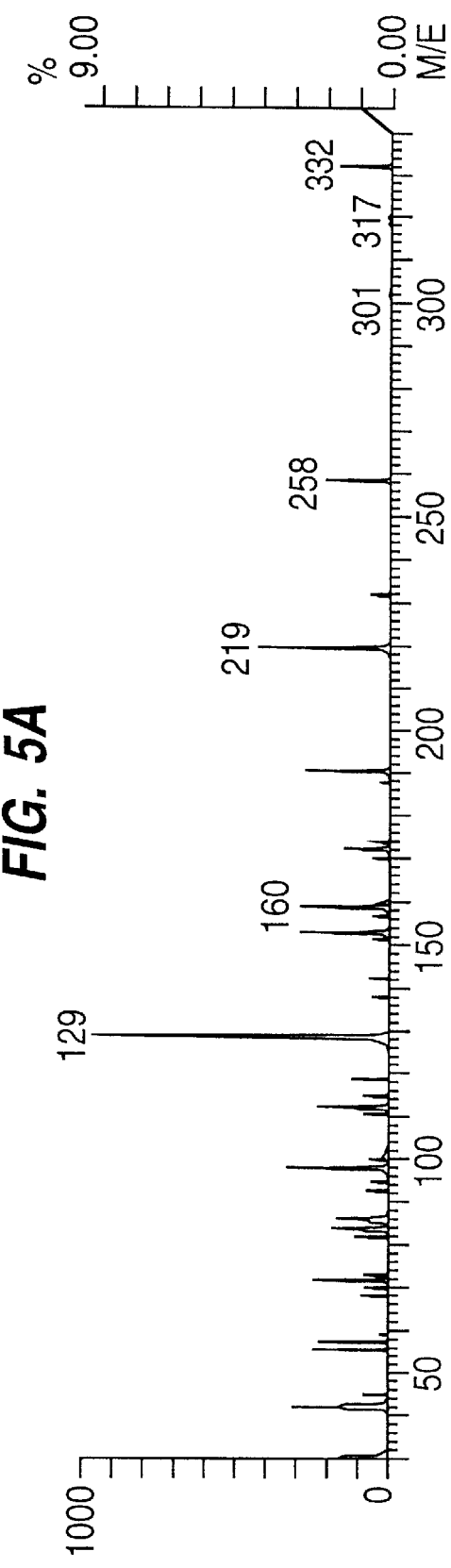
FIG. 5. MS spectrum of 1-N-ethylgentamicin $C_{1a}$.
Figure 5B:
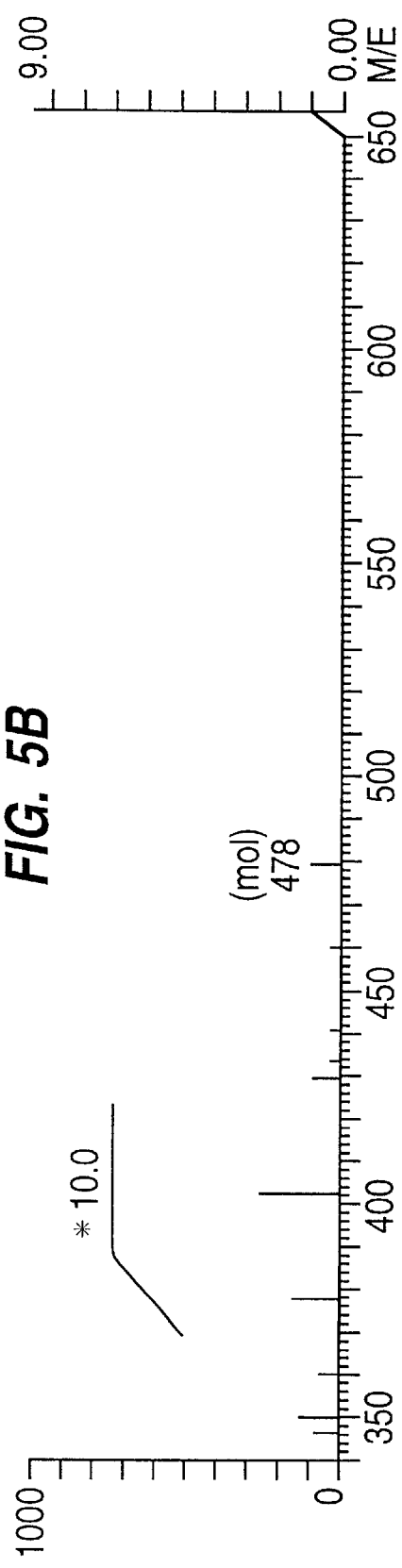
Figure 6:
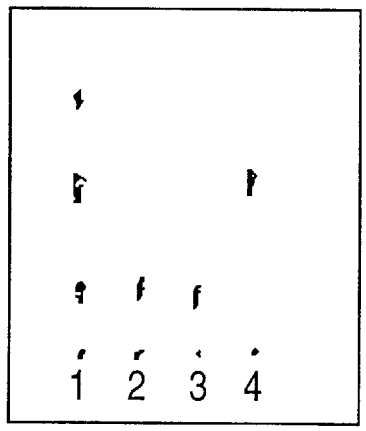
FIG. 6. TLC on silica gel chart of the product obtained by fermentation of *M.echinospora* mutant CGMCC0197.
Figure 7:
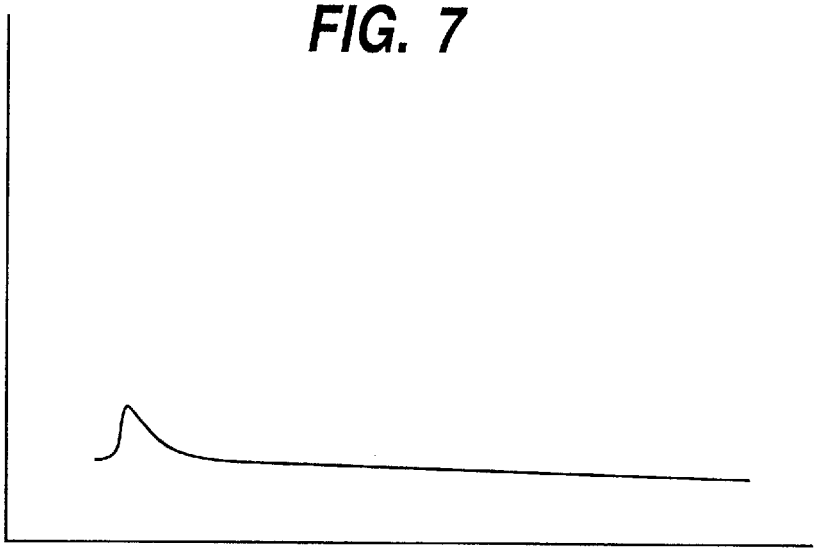
FIG. 7. UV spectrum of the product obtained by fermentation of *M.echinospora* mutant CGMCC0197.
Figure 8:
FIG. 8. IR spectrum of the product obtained by fermentation of *M.echinospora* mutant CGMCC0197.
Figure 9:
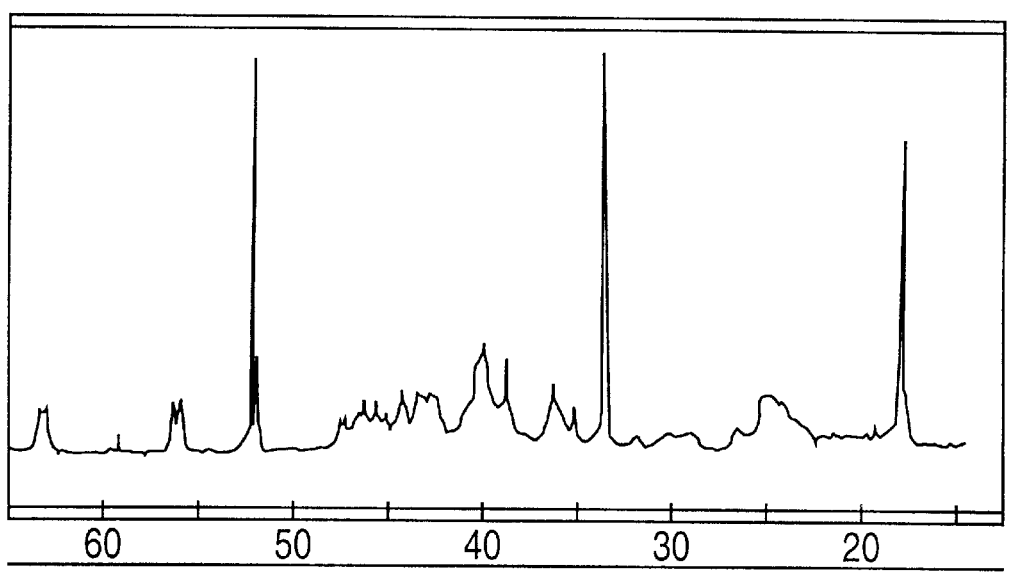
FIG. 9. NMR spectrum of the product obtained by fermentation of *M.echinospora* mutant CGMCC0197.

5. MS as shown in FIG. 5 was obtained by the use of ZAB-2F MS spectrometer.m/e of $(M+1)^+$ is 478, identical to molecular weight of $C_{21}H_{43}N_5O_7$ (the molecular formula of 1-N-ethylgentamicin $C_{1a}$). Also there is the character of m/e 317 and m/e 258 for 1-N-ethylgentamicin $C_{1a}$ (the character of 3-N-ethylgentamicin is m/e 289 and m/e 286).

Example 5 Preparation of 1-N-ethylgentamicin $C_{2b}$ (1) 3,2'-di-N-acetylgentamicin-$C_{2b}$ Lyophilized gentamicin $C_{2b}$ (1 g, 2.16 mmol) was dissolved in dimethyl sulfoxide (40 ml), and cobalt (II) acetate tetrahydrate (1.1 g, 4.52 mmol) was added with stirring at 25° C. After 20 min of stirring, a freshly prepared 1M solution of acetic anhydride in tetrahydrofuran (6.5 ml) was added dropwise. After 1 hr of stirring, the product was extracted from the mixture with cation exchange resin (e.g. 732 resin ($NH_4^+$)) and eluted with 2 mol·L$^{-1}$ ammonium hydroxide solution. The volume of the eluant was concentrated in vacuo to a volume of 30 ml, and hydrogen sulfide bubbled through the solution until all the cobalt was completely precipitated. The solids were removed by filtration. The filtrate were concentrated and lyophilized to give 3,2'-di-N-acetylgentamicin-$C_{2b}$ (1.05 g, 80% yield)

(2) 1-N-ethyl-3,2'-di-N-acetylgentamicin-$C_{2b}$ 3,2'-di-N-acetylgentamicin-$C_{2b}$ obtained above (1.05 g, 1.73 mmol, 90% purity) was dissolved in water (30 ml) and cooled to 3° C. with stirring, and the pH of the solution was brought to 2.5 by the addition of 1M hydrochloric acid. A freshly prepared 1M solution of acetaldehyde in tetrahydrofuran (2 ml) was added, stirred for 10 min. This was followed by a solution of sodium borohydride (95 mg, 2.50 mmol) in water (2 ml) which was added dropwise while maintaining the temperature at 3° C. The mixture was stirred for 1 hr. The pH was brought to 2.5 again by the addition of 1M hydrochloric acid. 0.2 ml of the above stock solution of acetaldehyde was added. After stirring of 5 min, sodium borohydride (16 mg, 0.42 mmol) dissolved in a little water was added dropwise. After 1 hr of stirring, the above process was repeated with 1M HCl, 0.20 ml of the acetaldehyde and 8 mg of sodium borohydride. After 2 hr of stirring, the mixture was evaporated in vacuo to 30 ml and the residue chromatographed on absorption resin (e.g.YPR-II resin) with solutions of 3%, 6%, 15% ethanol as the eluant. The eluates containing the product (the product spot was seen on TLC in the lower phase of chloroform-methane-ammonium hydroxide (2:1:1)) were pooled, concentrated and lyopillized to give 1-N-ethyl-3,2'-di-N-acetylgentamicin $C_{2b}$ (0.59 g, 86% purity,51% yield)

(3) 1-N-ethylgentamicin $C_{2b}$

1-N-ethyl-3,2'-di-N-acetylgentamicin $C_{2b}$ obtained above (0.59 g, 0.88 mmOl) was dissolved in 1M sodium hydroxide (100 ml) and the solution heated and hydrolyzed under reflux for 48 h until only the product spot was observed on TLC in a lower phase of chloroform: methane: 28% ammonium hydroxide (2:1:1)

Figure 11:
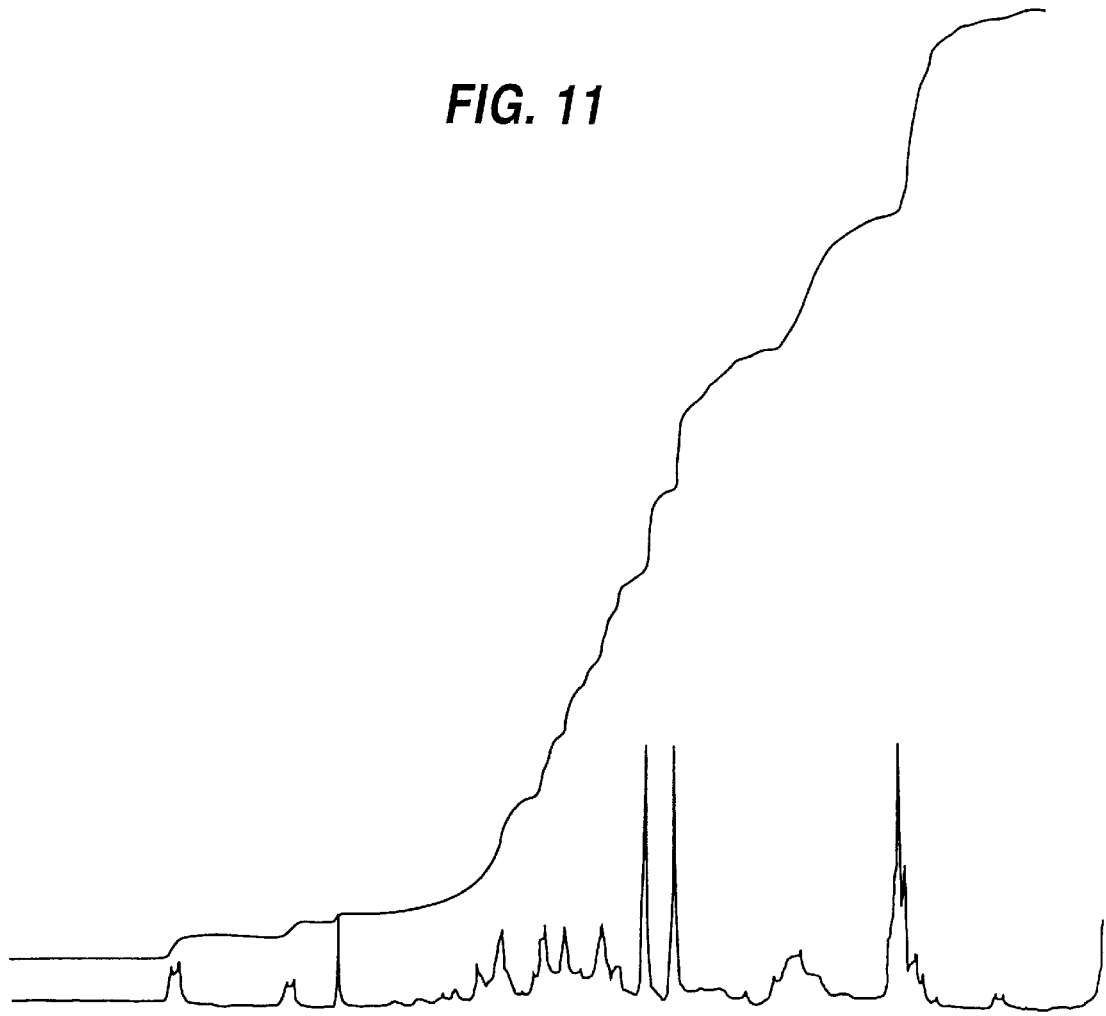
FIG. 11 is a NMR spectrum of 1-N-ethylgentamicin $C_{2b}$.

The mixture solution was adjusted to pH 6.0 by 3 mol/L $H_2SO_4$ and chromatographed on a column (1×30 cm) of absorbing resin (e.g.YPR-II resin) with solutions of 3% (50 ml), 6% (50 ml), 15% (100 ml) ethanol as the eluant. The eluates containing the product were pooled, evaporated in vacuo and lyophilized to give 1-N-ethylgentamicin $C_{2b}$ (0.3 g, 0.17 mmol, 91% purity, 82% yield). $^1$H-NMR ($D_2O$) as shown in FIG. 11: 1.22 (3H, 1-N-C-$CH_3$), 1.26 (3H, 4"-$CH_3$), 2.17 (3H, 1-N-C-$CH_3$), 2.95 (3H, 3"-N-$CH_3$), 5.17 (H, 1"-H), 5.85 (H,1'-H).

Example 6 Preparation of 1-N-ethylgentamicin $C_2$ (1) 3,2',6'-tri-N-acetylgentamicin $C_2$ Gentamicin $C_2$ (5 g, 10.6 mmol) was dissolved in dimethyl sulfoxide (200 ml), and cobalt (II) acetate tetrahydrate (5.4 g, 22 mmol) was added with stirring at 25° C., After 20 min of stirring, a freshly prepared 1M solution of acetic anhydride in tetrahydrofuran (28.5 ml) was added dropwise. After the addition was complete, the mixture was stirred for a further period of 1 h and diluted with water (250 ml). The product was adsorbed on a column (3×30 cm) of 110 cation exchange resin ($H^+$), washed with water to remove the organic solvent and eluted with 2 mol·L$^{-1}$ ammonium hydroxide. The eluates containing 3,2',6'-tri-N-acetylgentamicin C$_2$ were pooled, concentrated in vacuo. Hydrogen sulfide was bubbled through the concentrate until all the cobalt was completely precipitated. The solids were removed by filtration with diatomite as filter aid. The filtrate was concentrated and lyophilized to give 3,2',6'-tri-N-acetylgentamicin C$_2$ (5.8 g, 85% purity, 81% yield).

(2) 1-N-ethyl-3,2',6'-tri-N-acetylgentamicin C$_2$

The solution of 3,2',6'-tri-N-acetylgentamicin C$_2$ (4.5 g) in water (100 ml) was brought to a pH of 5.0 by the addition of 3M H$_2$SO$_4$, cooled to 3° C. in ice water bath and adjusted to a pH of 3.0 with 1M HCl. 6 ml of freshly prepared solution of 40% aqueous acetaldehyde-tetrahydrofuran (1:1) was added. The pH of mixture was brought to 4 by addition of 25% sodium cyanoborohydride aqueous solution which was added dropwise with stirring. The mixture was stirred and maintained at a pH of 3~4 for reaction for 1 hr. The above process was repeated three~four times until the 1-N-ethyl-3,2',6'-tri-N-acetylgentamicin C$_2$ spot was not observed on TLC in the lower phase of chloroform-methanol-ammonium hydroxide (2:1:1). The mixture was concentrated in vacuo to remove acetaldehyde and the residue was chromatographed on a column (25×300 mm) of CAD-40 resin with solutions of 3%, 8%, 15% ethanol (0.5 mol·L$^{-1}$ ammonium hydroxide) as the eluant. The eluates containing the product were pooled, concentrated and lyophilized to give 1-N-ethyl-3,2',6'-tri-N-acetylgentamicin C$_2$(3.2 g, 65% yield).

(3) 1-N-ethyl-gentamicin C$_2$

1-N-ethyl-3,2',6'-tri-N-acetylgentamicin C$_2$ (2.5 g) was dissolved in 1M sodium hydroxide (50 ml), and the solution heated under reflux for 48 h at 100° C. The solution was cooled, diluted to 500 ml with water and adjusted to a pH of 9 with 732 (H$^+$) ion-exchange resin. The resin was removed and poured into a column (3×15 cm) and eluted with 2 mol·L$^{-1}$ ammonium hydroxide. The eluate containing the product was concentrated in vacuo and the residue chromatographed on a column (2.5×30 cm) of CAD-40 adsorbing resin with solutions of 3%, 6%, 15% ethanol (0.5 mol·L$^{-1}$ ammonium hydroxide) as the eluant. The homogeneous fractions containing the product were pooled, concentrated and lyophilized to give 1-N-ethyl-gentamicin C$_2$ (1.4 g, 70% yield).

Example 7. Preparation of 1-N-ethylgentamicin C$_1$ (1) 3,2'-di-N-acetylgentamicin C$_1$ Gentamicin C$_1$ (0.477 g, 1 mmol) was dissolved in dimethylsulfoxide (20 ml), and cobalt (II) acetate tetrahydrate (0.55 g) was added with stirring at 25° C. After 20 min of stirring, a freshly prepared 1M solution of acetic anhydride in tetrahydrofuran (2.9 ml) was added dropwise. After the addition was complete, the mixture was stirred for a further period of 1 h and diluted with water (25 ml). The product was adsorbed on a column of 732 (H$^+$) cation exchange resin, washed with water and eluted with 2 mol·L$^{-1}$ ammonium hydroxide. The ammonium hydroxide extract was concentrated to 20 ml. Hydrogen sulfide was bubbled through the concentrate until all the cobalt was completely precipitated. The solid was removed by filtration. The filtrate was concentrated and lyophilized to give 3,2'-di-N-acetylgentamicin C$_1$ (0.55 g, 85% purity, 82% yield).

(2) 1-N-ethyl-3,2'-di-N-acetylgentamicin C$_1$

The solution of 3,2'-di-N-acetylgentamicin C$_1$ (0.45 g) in water (15 ml) was brought to a pH of 3 by the addition of 1M hydrochloric acid, cooled and maintained at 3° C. in ice water bath. A freshly prepared solution of 40% acetaldehyde-tetrahydrofuran (1:1, 0.84 ml) was added. After 10 min of stirring, 10% sodium cyanoborohydride aqueous solution was added dropwise. The pH of the mixture was maintained at 3~4 with 1 mol·L$^{-1}$ HCl. After 1 hour of stirring, the above process was repeated until the 3,2'-di-N-acetylgentamicin C$_1$ spot wasn't seen on TLC. The mixture was concentrated in vacuo to remove acetaldehyde and the residue was chromatographed on a column of YPR-II resin with solutions of 5%, 10%, 20% ethanol (0.5 mol·L$^{-1}$ ammonium hydroxide) as the eluant. The eluates containing the product were pooled, concentrated and lyophilized to give 1-N-ethyl-3,2'-di-N-acetylgentamicin C$_1$ (0.234 g, 48% yield).

(3) 1-N-ethyl-gentamicin C$_1$

The product above was dissolved in 30 ml of 1M sodium hydroxide and the solution was heated under reflux for 48 h until only the product spot was observed on TLC. As well as example 6 the extract was obtained, concentrated and residue chromatographed on a column of YPR-II adsorptive resin with solutions of 3%, 6%, 15% ethanol (0.5 mol·L$^{-1}$ ammonium hydroxide) as the eluant. The eluates containing the product were pooled, concentrated and lyophilized to give 1-N-ethyl-gentamicin C$_1$ (0.124 g, 63%).

Example 8. Preparation of 1-N-ethylgentamicin C$_{1a}$ Sulfate Injection

Injection used for clinic may be prepared with 1-N-ethylgentamicin C$_{1a}$ sulfate or its salts soluble in water.

| formulation | |
|---|---|
| injection solution | per injection |
| 1-N-ethylgentamicin C$_{1a}$ sulfate | 50 g (unit) |
| anhydrous sodium sulphite | 2 g |
| Water for injection | added to 1.0 L |
| pH | 5.0 ~ 7.0 |

Procedure: place approximately 80% volume of water for injection to a suitable vessel. Charge and dissolve anhydrous sodium sulphite and 1-N-ethylgentamicin C$_{1a}$ sulfate, adjust the pH of the solution and add appropriate amount of activated charcoal. Bring the batch volume to 1 Liter with the addition of water for injection and agitate for homogenization. Remove activated charcoal by filtration under sterile condition, and filter the solution through a suitable bacteria retentive filter. Fill the filtrate aseptically into pyrogen-free closed vials, fill nitrogen, seal and sterilize.

In the formulation above, sodium pyrosulphite as antioxidant and add methyl 4-hydroxybenzoate (1.3 mg/50 mg potency component) and propyl 4-hydroxybenzoate (0.2 mg/50 mg potency component) as antiseptic may also be added.

Specification:

50 mg(unit)/1 ml 75 mg(unit)/1.5 ml 100 mg(unit)/2 ml

Example 9. Preparation of Freeze-Dried Powder of 1-N-ethylgentamicin C$_{1a}$ for Injection

| formulation | per injection |
|---|---|
| 1-N-ethylgentamicin C$_{1a}$ sulfate | 50 mg (unit) |
| sodium chloride | 9 mg |
| Dextran (low molecular wt) | 7 mg |
| sodium pyrosulphite | 3 mg |
| water for injection | 0.5 ml |

Procedure: charge approximately 70% volume of water for injection to a suitable vessel. Dissolve sodium pyrosulphite (A.R), sodium chloride, and 1-N-ethylgentamicin C$_{1a}$ sulfate in order and add a solution of Dextran (low molecular wt). Bring the solution to its final volume with the addition of water for injection and agitate until homogeneous. Filter the solution twice through a bacteria retentive filter (filter membrane of 0.22 μm micropores). Fill 0.5~0.54 ml of filtrate aseptically into a pyrogen-free ampoule. Freeze-dry and seal.

Example 10. Preparation of 1-N-ethylgentamicin $C_{1a}$ Tablet (including sustained release form and enteric form)

|  | 100 mg (unit) per tablet per 100,000 tablets |
|---|---|
| formulation I | |
| 1-N-ethylgentamicin $C_{1a}$ (as the sulfate) | 10 kg |
| sucrose | 12.4 kg |
| calcium carbonate | 6.8 kg |
| starch | 5 kg |
| citric acid | 0.3 kg |
| ethanol (70%) | 8 L |
| magnesium stearate | 0.4 kg |
| formulation II | |
| 1-N-ethylgentamicin $C_{1a}$ (as the sulfate) | 5 kg |
| dextrin | 4.7 kg |
| 20% starch paste | suitable |

Procedure: charge and agitate until homogeneous. Spray dry the slurry. Add the corn starch and 1% weight of magnesium stearate, and mix, compress into tablets using suitable tableting equipment.

indications: dysentery, enteritis and diarchea caused by bacteria.

Example 11 Preparation of 1-N-ethylgentamicin $C_{1a}$ Eye Drops

| formulation | |
|---|---|
| 1-N-ethylgentamicin $C_{1a}$ (as the sulfate) | 5 g (unit) |
| sodium chloride | 8 g |
| sodium pyrosulphite | 2 g |
| distilled water | added to 1000 ml |

Procedure:

Place 70% of distilled water into a suitable mixing vessel. Add sodium chloride and sodium pyrosulphite and mix until dissolved. Add 1-N-ethylgentamicin $C_{1a}$ sulfate and mix again until dissolved. Adjust its pH to 7.0 with 0.5N sodium hydroxide. Bring the solution to its final volume by the addition of distilled water. Pass the solution through a suitable sterilizing filter. Fill the solution into a suitable sterile dropping bottle, seal and sterilize.

indications: conjunctivitis, pinkeye disease etc. caused by bacteria.

Example 12 Preparation of 1-N-ethylgentamicin $C_{1a}$ Liniment

| formulation | |
|---|---|
| 1-N-ethylgentamicin $C_{1a}$ (as the sulfate) | 1.6 g |
| Liquid paraffin | 3.3 g | indication: abscess, pyoderma, scalding, burn wound and other infections on skin caused by bacteria.

Example 13 Preparation of 1-N-ethylgentamicin $C_{1a}$ aerosol

| formulation | |
|---|---|
| 1-N-ethylgentamicin $C_{1a}$ | 10 mg |
| ethanol | 4.5 mg |
| Dichlorodifluoromethane | appropriate amount 14 ml/tin | indications: tracheitis, tonsiltitis and angina etc caused by bacteria.

Example 14 Preparation of 1-N-ethylgentamicin $C_{1a}$ ointment (emulsifying form base)

| formulation 1 | (oil/water form base) |
|---|---|
| 1-N-ethylgentamicin $C_{1a}$ (as the sulfate) | 1.6 g |
| emulsifying wax | 30 g |
| white petroleum | 50 g |
| Liquid paraffin | 20 g |
| formulation 2 | (water/oil form base) |
| 1-N-ethylgentamicin $C_{1a}$ (as the sulfate) | 1.6 g |
| polyglycerine stearate | 6 g |
| vaseline | 96.8 g |
| formulation 3 | (water-soluble base) |
| 1-N-ethylgentamicin $C_{1a}$ (as the sulfate) | 1.6 g |
| gelatin | 3 g |
| glycerine | 3 g |
| distilled water | appropriate amount final weight 100 g |

In the examples 8~14 above, 1-N-ethylgentamicin $C_{1a}$ as the active component may be replaced by 1-N-ethylgentamicin $C_{2b}$, or 1-N-ethylgentamicin $C_1$ or 1-N-ethylgentamicin $C_2$ to form corresponding compositions.

INDUSTRIAL APPLICABILITY

The advantages of this invention are obvious. *Micromonospora echinospora* mutant CGMCC0197 provided by this invention can produce gentamicin $C_{1a}$ more than 800 ug per milliliter broth. Thus, this invention provides a biosynthetic process of producing $GMC_{1a}$ through mutation of gene. The *Micromonospora echinospora* mutant CGMCC0197 has a high productive potency. Thus, it can be used directly to provide useful mother nucleus for the preparation of 1-N-ethyl-gentamicin $C_{1a}$ by this invention. Derivatives of gentamicin provided by this invention or their salts and the compositions consisting of them as active components and some pharmaceutically acceptable additives are broad spectrum antibiotics. Specially, 1-N-ethyl-gentamicin $C_{1a}$ is active against gentamicin-resistant strains and has a lower ototoxicity and nephrotoxicity. It is suitable for curing septicaemia, bronchitis, bronchiectasis, pneumonia, peritonitis, pyelonephritis, cystitis caused by those bacteria susceptible to this drug such as *P. aeruginosa, proteus. sp.,* Serratia and those bacteria resistant to Gentamicin (GM), Kanamycin (KM), Methicillin, Amikacin (AMK) such as *Escherichia coli,* Klebsiella and Staphylococcus. It is also applicable to patients who are allergic to penicillin, specially to the old and children. It is safer than gentamicin, kanamycin and amikacin. It could be the first choice for curing infections caused by those strains resistant to GM, KM, Micronomicin (MCR) and methicillin. It shows no cross-resistance with AMK, and thus it can be used to treat infections caused by AMK-resistant bacteria.

The in vitro study of its antibacterial and germicide effects on 1108 common pathogenic bacteria shows that the antibacterial activity of 1-N-ethyl-gentamicin $C_{1a}$ is similar or superior to gentamicin. The MIC values of half or more than half of GM-resistant, MCR-resistant and cefazolin-resistant strains are within its effective serum concentration range. Particularly, at a concentration of 8 mg·L$^{-1}$ or less, it could inhibit 66 percent of 53 highly-resistant strains of S.aureus. Therefore, 1-N-ethyl-gentamicin $C_{1a}$ of this invention enhances the activity against methicillin-resistant S.aureus (MRSA) (see table 4~7).

In vivo, 1-N-ethyl-gentamicin $C_{1a}$ shows good therapeutic effects on bacteria infected mice. Its in vivo protecting action is similar to AMK, but superior to GM and Tobramycin, while inferior to 1-N-ethyl-sisomicin. Its therapeutic effect in vivo on GM-resistant strains infected mice is 2 to 5 times as much as AMK, GM and Tobramycin.

The therapeutic effects of 1-N-ethyl-gentamicin $C_{1a}$ of this invention on infected mice show good reproducibility. The study on the culture of the heart blood of survival mice shows that 1-N-ethyl-gentamicin $C_{1a}$ has good negative-turning ratio. That is, it has high inhibitive activities and germicide activities in vivo which are similar to those in vitro.

Results of toxicological study of 1-N-ethyl-gentamicin $C_{1a}$

1. Acute toxicity of 1-N-ethyl-gentamicin $C_{1a}$

To Kunming mice, the $LD_{50}$ of 1-N-ethyl-gentamicin $C_{1a}$ administrated by i.v., s.c., i.m. were 65.47, 479.91, 172.89 mg/kg respectively; To NIH mice, the $LD_{50}$ administrated by i.v., s.c. were 79.88 mg/kg and 460.42 mg/kg respectively. The acute toxicity of 1-N-ethyl-gentamicin $C_{1a}$ was lower than that of netilmicin obviously and similar to that of GM.

To rat, the $LD_{50}$ of 1-N-ethyl-gentamicin $C_{1a}$ administrated by i.v., s.c., i.m., i.p. were 73.75, 402.65, 565.16 and 627.98 mg/kg respectively.

2. Chronic toxicity of 1-N-ethyl-gentamicin $C_{1a}$

In order to evaluate the safety of consecutive administration of 1-N-ethyl-gentamicin $C_{1a}$, the toxicity after administration to rat by i.p. for 90 days and after administration by i.v. to Beagle dog for 90 days were examined.

In the test, 30,100,180 mg/kg·day(MKD) of 1-N-ethyl-gentamicin $C_{1a}$ were administrated by i.p. to rats respectively as lower median and high doses. Physiological observation, hematological and pathological examinations were taken. The result of the test shows that the dosage of 1-N-ethyl-gentamicin showing apparent intoxication and of general safety were 100 MKD and 30 MKD respectively, compared with 63 MKD and 25 MKD of MCR. That is, the chronic toxicity of 1-N-ethyl-gentamicin $C_{1a}$ is not greater than that of MCR.

Three groups of Beagles were intravenously administrated for 90 days respectively at 10, 30, 60 MKD. The eye ground was examined besides the three examinations above. The results were compared with that of MCR in literature. Result of 1-N-ethyl-gentamicin $C_{1a}$ administrated i.v. for 90 days is similar to that of MCR administrated i.m. for 30 days. Thus, in clinically research of 1-N-ethyl-gentamicin $C_{1a}$, the clinical dosage of MCR could be a useful reference.

3. Ototoxicity

Rat pinna reflex model and mice swimming test model were used to investigate the ototoxicity of 1-N-ethyl-gentamicin $C_{1a}$, GM and KM. The result shows that the ototoxicity of gentamicin $C_{1a}$ is much lower than those of GM and KM.

Comparison of ototoxicity to guinea pig of 1-N-ethyl-gentamicin $C_{1a}$, with GM and AMK: In the test, three dosage levels were offered (for each group, administrated i.m., once a day for 28 days). The hearing and vestibule function were determined during the experiment. The guinea pig was guillotined the next day after the last injection for detection of the hearing and vestibule function. Temporal bone was fixed to make inner ear specimen and whole surface preparation of cochlea, the number of necrotized hair cells was counted, the morphology was observed by scanning electron micrograph.

The result of the test is as follows:

(1) Cochleatoxicity: compared with physiological saline control group, no apparent cochleatoxicity of 1-N-ethyl-gentamicin $C_{1a}$ was observed at all three dosages; for gentamicin and amikacin, increases of ABR threshold were observed at middle dosages, while nearly all the auditory function of the animals were lost at high dosages. In the 1-N-ethyl-gentamicin $C_{1a}$ group, there was not any change of morphology of hair cell of the animals, the spiral nerves being normal. Even at the dosage of 100 mg/kg/day, the corti's organ was completely normal. No cochleatoxicity of 1-N-ethyl-gentamicin $C_{1a}$ was observed in the dosage range of this test. In gentamicin and amikacin groups, cochleatoxicity were observed at all three dosages, even at low and middle dosages, scattered necrotized hair cell and scar formation were observed. At high dosage, large number of necrotized hair cell, even stand cell and nerve cell were observed. Thus, 1-N-ethyl-gentamicin $C_{1a}$ has little toxicity to cochlea, while gentamicin and amikacin cause observable injury to cochlea.

(2) Vestibuletoxicity: All three drugs show differences, compared with the control group. In the group administrated with 1-N-ethyl-gentamicin $C_{1a}$, only at high dosages did the inhibition ratio of oculi fremitus increase and the topagno hair cells in ellipse-bundle burl and crista ampullaris adhere to each other, but colloid membranes remaining intact. In the groups administrated with GM or AMK, vestibule function was impaired and morphology affected, and at high dosages, colloid membrane and topagno hair cells in the center of ellipse-bundle burl disappeared and a little remaining topagno hair cells adhered to each other. Calculus auralis waned or blurred, topagno hair cells on the ball-bundle burl were incomplete or disappeared. Thus, 1-N-ethyl-gentamicin $C_{1a}$ has the lowest vestibuletoxocity, KM the median, and GM the highest.

Considering all the above, it can be concluded that 1-N-ethyl-gentamicin $C_{1a}$ has very little ototoxicity.

4. Nephrotoxicity of 1-N-ethyl-gentamicin $C_{1a}$

1-N-ethyl-gentamicin $C_{1a}$ is an aminoglycoside antibiotic. The kidney is one of the target organ of toxicity. Six indexes of urine, two indexes of blood biochemistry combined with the observation of the pathology and morphology of the kidney were examined to compare the nephrotoxicities of 1-N-ethyl-gentamicin $C_{1a}$, AMK and GM to rat after i.m. administration. In all three test groups, the number of normal indexes increased and the pathology changes worsened with the increase of dosing interval and dosages. From the seventh day of administration, the number of dead animals in the groups administrated with 150 MKD and 100 MKD gentamicin gradually increased. There were no dead in the groups administrated with 1-N-ethyl-gentamicin $C_{1a}$ and amikacin. So the comparison of nephrotoxicity among the three drugs can be made only at the low dosage of 50 MKD. In the group administrated with gentamicin at the dose of 50 MKD for 5~15 days, the number of abnormal indexes increased from three (LU-LDH, U-Pr, BUN) to six (LU-GOT, U-LDH, U-Pr, U-Su, BUM, Scr). The necrosis also expanded from single scattered necrosis of the epithelial cell of renal ductule after 5 days administration to extent serious necrosis of the kidney. In the group injected with 1-N-ethyl-gentamicin $C_{1a}$ and AMK at the same dosage, only a few indexes turned to be abnormal in statistics or showed a little increase. In morphology, the injury only expanded from slight denaturation to single scattered necrosis of cell. According to the result of comparison of function and morphology, the nephrotoxicity of 1-N-ethyl-gentamicin $C_{1a}$ is far lower than that of gentamicin and similar to that of AMK.

5. A Ame's test of 1-N-ethyl-gentamicin $C_{1a}$ turned to be negative, and a study of reproduction toxicity showed that 1-N-ethyl-gentamicin $C_{1a}$ has no embryotoxicity. The investigation of pharmacokinetics and its distribution in animal organs indicate that 1-N-ethyl-gentamicin $C_{1a}$ can be absorbed rapidly and has a short half-life elimination. The drug serum concentration increases with the dosage. 1-N-ethyl-gentamicin $C_{1a}$ was excreted mainly through the kidney. A high concentration of 1-N-ethyl-gentamicin $C_{1a}$ was found in kidney, somewhat lower concentrations were detected in lung, heart and spleen. It is worth note that 1-N-ethyl-gentamicin $C_{1a}$ was found to penetrate into the cerebral tissue more readily than GM. This makes 1-N-ethyl-gentamicin $C_{1a}$ more valuable in clinical use. Its binding with serum protein is low.

The examples above are given only for explanation. The range of protection for this invention will be defined in the claims.

TABLE 2

Comparison of physiological-biochemical properties between JIM-202 (CGMCC 0197) and JIM-401

| Item | JIM-202 (CGMCC 0197) | JIM-401 |
| --- | --- | --- |
| Hydrolysis of starch | Positive | Positive |
| Reduction of nitrate | Positive | Negative |
| Peptonization of skimmed milk | Coagulated, well peptonized | Poorly peptonized |
| Liquefaction of gelatin | Well | Negative |
| Tyrosinase reaction | Good | Poor |
| Digestion of cellulose | Good | Negative |

TABLE 3

Comparison of carbon source utilization between JIM-202 (CGMCC 0197) and JIM-401

| Carbon source | JIM-202 (CGMCC 0197) | JIM-401 |
| --- | --- | --- |
| D-xylose | + | ± |
| D-arabinose | + | − |
| L-rhamnose | + | ± |

TABLE 1

Comparison of cultural characters between JIM-202 AND JIM-401 on ten agar media

| Medium | Spore | Substrate mycelium | Soluble pigment |
| --- | --- | --- | --- |
| | | JIM-202 (CGMCC 0197) | |
| Glucose-asparagine agar | Black | Little poor, grayish white II 81' | None |
| Glucose-yeast ext. agar | Black | Moderate, black II 31' | None |
| Starch-asparagine agar | Black | Good, black | Blue black |
| Czapek's agar | Black | Good | Blackish |
| Peptone-Fe agar | Black, a few | Poor, blackish | None |
| Bennet's agar | Brownish black | Moderate, dark reddish brown V 76' | Light brownish |
| Potatoes block | Black, a few | Poor, black | None |
| Potatoes block + CaCO₃ | Blackish, a few | Poor, blackish | None |
| Wheat bran agar | VII 73', a few | VII 62' | Light purplish |
| Emerson's agar | Elephant gray, IV 71' | Moderate, reddish brown V 75' | Brownish black |
| | | JIM-401 | |
| Glucose-asparagine agar | None | Pour, wine purple (VII 75') | None |
| Glucose-yeast ext. agar | None | Moderate, wrinkled, light cinnamon (III 55'–IV 65') | None |
| Starch-asparagine agar | Few, black | Moderate IV 64', IV 65' | Very little |
| Czapek's agar | Black | Good, black | Dark brown |
| Peptone-Fe agar | Few, brownish purple | Poor, III 14' | None |
| Bennet's agar | None | Reddish, purple (VII 77') | Very little |
| Potatoes block | None | None | None |
| Potatoes block + CaCO₃ | None | (V 47') | None |
| Wheat bran agar | Few, purplish black | Moderate (X 72') | Very little |
| Emerson's agar | None | Wrinkled (VII 64"–VII 77') | None |

TABLE 3-continued

Comparison of carbon source utilization between JIM-202 (CGMCC 0197) and JIM-401

| Carbon source | JIM-202 (CGMCC 0197) | JIM-401 |
|---|---|---|
| D-galactose | + | ± |
| Raffinose | + | ± |
| D-fructose | + | ± |
| Sucrose | + | ± |
| Mannose | + | − |
| Inositol | + | − |
| D-melibiose | + | / |
| Glucose | + | ± |

TABLE 4

Antibacterial activity of 1-N-ethylgentamicin C1a against 1108 strains pathogenic bacteria

| Organism (No.) | $MIC_{50}$ | $MIC_{90}$ | Mode MIC | MIC range |
|---|---|---|---|---|
| Pseudomonas sp. (204) | 8 | >256 | 8 | 0.125–>256 |
| Enterobacter cloacae (29) | 2 | 64 | 0.25 | 0.25–>256 |

TABLE 4-continued

Antibacterial activity of 1-N-ethylgentamicin C1a against 1108 strains pathogenic bacteria

| Organism (No.) | $MIC_{50}$ | $MIC_{90}$ | Mode MIC | MIC range |
|---|---|---|---|---|
| Serratia sp. (30) | 0.5 | 32 | 0.5 | 0.062–256 |
| Proteus mirabilis (60) | 0.5 | 2 | 0.5 | 0.125–128 |
| Haemophilus influenzae (8) | 0.031 | 4 | 0.031 | 0.031–4 |
| Streptococcus viridans (27) | 1 | 4 | 2 | 0.062–4 |
| Streptococcus pneumoniae (14) | 0.25 | 4 | 0.031 | 0.031–16 |
| Staphylococcus epidermidis (27) | 0.31 | 1 | 0.031 | 0.031–16 |
| Staphylococcus arueus (190) | 1 | 16 | 0.062 | 0.031–128 |
| Streptococcus faecalis (33) | 32 | 256 | 1 | 0.5–256 |
| Streptococcus pyogenes (27) | 1 | 32 | 1 | 0.25–128 |
| Methicillin resistant S. aureus (53) | 8 | 32 | 8 | 0.5–128 |

TABLE 5

Comparison of MIC and MBC between 1-N-ethylgentamicin $C_{1a}$ and Gentamicin

| Strain | Number | 1-N-ethylgentamicin $C_{1a}$ | | | | Gentamicin | | | |
|---|---|---|---|---|---|---|---|---|---|
| | | $MIC_{50}$ | $MBC_{50}$ | $MIC_{90}$ | $MBC_{90}$ | $MIC_{50}$ | $MBC_{50}$ | $MIC_{90}$ | $MBC_{90}$ |
| Pseudomonas sp. | 2 | 1 | 2 | 4 | 8 | 2 | 2 | 4 | 8 |
| S. aureus | 31 | 0.062 | 0.5 | 0.25 | 2 | 0.125 | 0.5 | 0.5 | 2 |
| Escherichia coli | 20 | 0.125 | 0.25 | 0.5 | 1 | 0.125 | 0.5 | 0.25 | 1 |
| Klebsiella pneumoniae | 20 | 0.125 | 0.25 | 0.125 | 0.5 | 0.125 | 0.25 | 0.25 | 1 |
| Shigella | 10 | 0.062 | 0.5 | 0.125 | 1 | 0.125 | 0.25 | 0.25 | 1 |

TABLE 6

Comparison of MBC among 1-N-ethylgentamicin $C_{1a}$, Gentamicin Kanamicin, Amikacin

| Strain | Number | 1-N-ethylgentamicin | | Gentamicin | | Kanamicin | | Amikacin | |
|---|---|---|---|---|---|---|---|---|---|
| | | $MBC_{90}$ | MBC range | $MBC_{90}$ | MBC range | $MBC_{90}$ | MBC range | $MBC_{90}$ | MBC range |
| Pseudomonas sp. | 20 | 8 | 0.25–16 | 8 | 0.5–16 | 128 | 2–256 | 64 | 1–64 |
| S. aureus | 31 | 2 | 0.062–4 | 2 | 0.062 | 64 | 0.125–128 | 32 | 0.125–128 |
| Escherichia coli | 20 | 1 | 0.125–8 | 1 | 0.125–8 | 8 | 0.5–128 | 2 | 0.25–8 |
| Klebsiella pneumoniae | 20 | 0.5 | 0.062–1 | 1 | 0.062–2 | 4 | 0.25–4 | 1 | 0.125–2 |
| Shigella | 10 | 1 | 0.125–1 | 1 | 0.125–1 | 2 | 0.5–4 | 0.5 | 0.25–1 |

TABLE 4-continued

Antibacterial activity of 1-N-ethylgentamicin C1a against 1108 strains pathogenic bacteria

| Organism (No.) | $MIC_{50}$ | $MIC_{90}$ | Mode MIC | MIC range |
|---|---|---|---|---|
| Enterobacter aerugenes (27) | 0.25 | 16 | 0.125 | 0.062–32 |
| Escherichia coli (146) | 0.25 | 16 | 0.25 | 0.125–64 |
| Klebsiella pneumoniae (115) | 0.125 | 8 | 0.125 | 0.062–128 |
| Salmonella typhi (58) | 0.5 | 8 | 0.5 | 0.062–32 |
| Shigella dysenteriae (60) | 0.25 | 0.5 | 0.25 | 0.125–64 |
| Acinetobacter sp. (27) | 0.5 | 256 | 0.25 | 0.125–256 |
| Ciltrobacter sp. (30) | 0.25 | 16 | 0.25 | 0.125–128 |

TABLE 7

Comparison of MIC value to 53 methicillin resistant S. aureus (MRSA) between 1-N-ethylgentamicin $C_{1a}$ and other antibiotics

| No. | Medicin resistant bacteria No. | Methicillin | Oxacillin | Cefazolin | Gentamicin | 1-N-ethylgentamicin $C_{1a}$ |
|---|---|---|---|---|---|---|
| 1 | 91–131 | 128 | 128 | 128 | 32 | 8 |
| 2 | 106 | >256 | >256 | 128 | 32 | 16 |
| 3 | 528 | >256 | >256 | 128 | 32 | 8 |
| 4 | 281 | >256 | >256 | 128 | 16 | 4 |
| 5 | 1124 | 128 | >256 | 64 | 32 | 8 |

TABLE 7-continued

Comparison of MIC value to
53 methicillin resistant S. aureus (MRSA) between
1-N-ethylgentamicin $C_{1a}$ and other antibiotics

| No. | Medicin resistant bacteria No. | Methicillin | Oxacillin | Cefazolin | Gentamicin | 1-N-ethylgentamicin $C_{1a}$ |
|---|---|---|---|---|---|---|
| 6 | 210 | 32 | 32 | 32 | >256 | 32 |
| 7 | 1044 | 256 | 256 | 64 | 64 | 1 |
| 8 | 480 | >256 | >256 | 128 | 32 | 4 |
| 9 | 525 | 32 | 32 | 32 | 16 | 8 |
| 10 | 1057 | 128 | 256 | 32 | 128 | 16 |
| 11 | 1140 | 256 | 128 | 32 | 16 | 4 |
| 12 | 126 | 128 | 128 | 32 | 32 | 8 |
| 13 | 134 | 64 | 64 | 16 | 32 | 16 |
| 14 | 57 | 128 | 128 | 32 | 32 | 8 |
| 15 | 912 | 128 | 128 | 32 | 32 | 16 |
| 16 | 624 | >256 | >256 | 32 | >256 | 32 |
| 17 | 130 | 128 | 128 | 64 | >256 | 64 |
| 18 | 408 | 256 | >256 | 64 | 32 | 2 |
| 19 | 124 | 128 | 128 | 64 | 32 | 8 |
| 20 | 351 | 128 | 128 | 64 | 8 | 4 |
| 21 | 58 | 256 | 128 | 128 | 32 | 8 |
| 22 | 259 | >256 | >256 | 256 | 32 | 8 |
| 23 | 92–20 | >256 | >256 | >256 | 16 | 8 |
| 24 | 22 | 64 | 32 | 64 | 32 | 16 |
| 25 | 24 | >256 | >256 | >256 | 16 | 2 |
| 26 | 107 | >256 | 256 | 128 | 16 | 64 |
| 27 | 85 | >256 | >256 | 256 | 16 | 16 |
| 28 | 90 | 64 | 16 | 32 | 32 | 8 |
| 29 | 50 | >256 | 256 | 128 | 32 | 16 |
| 30 | 92–49 | >256 | >128 | 128 | 32 | 32 |
| 31 | 70 | >256 | >256 | 128 | 16 | 4 |
| 32 | 73 | >256 | >256 | 256 | 16 | 4 |
| 33 | 75 | >256 | 256 | 256 | 16 | 8 |
| 34 | 40 | >256 | >256 | 128 | 32 | 16 |
| 35 | 43 | >256 | >256 | 256 | 16 | 8 |
| 36 | 44 | >256 | >256 | 256 | 16 | 8 |
| 37 | 45 | >256 | >256 | 128 | 16 | 8 |
| 38 | 91 | >256 | >256 | 256 | 16 | 4 |
| 39 | 89 | >256 | >256 | 128 | 16 | 4 |
| 40 | 106 | >256 | >256 | 128 | 64 | 16 |
| 41 | 79 | >256 | >256 | 128 | 16 | 1 |
| 42 | 19 | 64 | 16 | >256 | 32 | 16 |
| 43 | 93 | >256 | >256 | 256 | 16 | 4 |
| 44 | 116 | >256 | >256 | 256 | 32 | 16 |
| 45 | 77 | >256 | >256 | 256 | >256 | 128 |
| 46 | 80 | >256 | >256 | 256 | 16 | 8 |
| 47 | 84 | >256 | >256 | 128 | >256 | 32 |
| 48 | 111 | >256 | >256 | 256 | 16 | 8 |
| 49 | 110 | >256 | >256 | 256 | 16 | 8 |
| 50 | 334 | >256 | >256 | 64 | 16 | 4 |
| 51 | 55 | >256 | >256 | 32 | 16 | 1 |
| 52 | 347 | 64 | 256 | 128 | 16 | 8 |
| 53 | 495 | 64 | 256 | 128 | 64 | 0.5 |

We claim:

1. *Micromonospora echinospora* strain CGMCC0197, which strain produces monocomponent gentamicin $C_{1a}$, of formula (I)

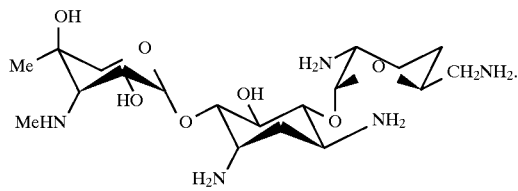

2. A method of producing semisynthetic 1-N-ethylgentamicin $C_{1a}$, comprising:

(a) producing monocomponent gentamicin $C_{1a}$ by fermenting *Micromonospora echinospora* mutant CGMCC0197, and recovering gentamicin $C_{1a}$ from the fermentation broth; and (b) selectively ethylating the 1-amino group of the gentamicin $C_{1a}$, and recovering the resultant 1-N-ethylgentamicin $C_{1a}$.

3. The method of claim 2, wherein gentamicin $C_{1a}$ from the fermentation broth is extracted and purified using either or both of a cation exchange resin and an adsorbing resin.

4. The method of claim 3, wherein primary amino groups of the gentamicin $C_{1a}$ recovered from the fermentation broth, other than the 1-amino group, are selectively protected in an aprotic polar solvent prior to said N-ethylation, and the protected gentamicin $C_{1a}$ is then extracted using a cation exchange resin.

5. The method of claim 4, wherein the isolated protected gentamicin $C_{1a}$ is N-ethylated by reaction with acetaldehyde and hydrogenation of the intermediate Schiff base, and the resultant protected 1-N-ethyl gentamicin $C_{1a}$ is deprotected to produce said resultant 1-N-ethyl gentamicin $C_{1a}$.

6. The method of claim 5, wherein said resultant 1-N-ethylgentamicin $C_{1a}$ is extracted from the reaction mixture using an adsorbing resin.

7. The method of claim 2, wherein primary amino groups of the gentamicin $C_{1a}$ recovered from the fermentation broth other than the 1-amino group, are selectively protected in an aprotic polar solvent prior to said N-ethylation, and the protected gentamicin $C_{1a}$ is then isolated using a cation exchange resin.

8. The method of claim 7, wherein the isolated protected gentamicin $C_{1a}$ is N-ethylated by reaction with acetaldehyde and hydrogenation of the intermediate Schiff base, and the resultant protected 1-N-ethyl gentamicin $C_{1a}$ is deprotected to produce said resultant 1-N-ethyl gentamicin $C_{1a}$.

9. The method of claim 8, wherein said resultant 1-N-ethylgentamicin $C_{1a}$ is extracted from the reaction mixture using an adsorbing resin.

10. A method of producing an antibacterial composition comprising semisynthetic 1-N-ethylgentamicin $C_{1a}$ or a pharmaceutically acceptable acid addition salt thereof, comprising:

(a) producing monocomponent gentamicin $C_{1a}$ by fermenting *Micromonospora echinospora* strain CGMCC0197, and recovering gentamicin $C_{1a}$ from the fermentation broth;

(b) selectively ethylating the 1-amino group of the gentamicin $C_{1a}$, and recovering the resultant 1-N-ethylgentamicin $C_{1a}$, and (c) combining a pharmaceutically effective amount of the 1-N-ethylgentamicin $C_{1a}$ or acid addition salt thereof with a pharmaceutically acceptable carrier to produce an antibacterial composition.

11. The method of claim 10, wherein gentamicin $C_{1a}$ from the fermentation broth is extracted and purified using either or both of a cation exchange resin and an adsorbing resin.

12. The method of claim 11, wherein primary amino groups of the gentamicin $C_{1a}$ recovered from the fermentation broth, other than the 1-amino group, are selectively protected in an aprotic polar solvent prior to said N-ethylation, and the protected gentamicin $C_{1a}$ is then extracted using a cation exchange resin.

13. The method of claim 12, wherein the isolated protected gentamicin $C_{1a}$ is N-ethylated by reaction with acetaldehyde and hydrogenation of the intermediate Schiff base, and the resultant protected 1-N-ethyl gentamicin $C_{1a}$ is deprotected to produce said resultant 1-N-ethyl gentamicin $C_{1a}$.

14. The method of claim 13, wherein said resultant 1-N-ethylgentamicin $C_{1a}$ is extracted from the reaction mixture using an adsorbing resin.

15. The method of claim 10, wherein primary amino groups of the gentamicin $C_{1a}$ recovered from the fermentation broth, other than the 1-amino group, are selectively protected in an aprotic polar solvent prior to said N-ethylation, and the protected gentamicin $C_{1a}$ is then isolated using a cation exchange resin.

16. The method of claim 15, wherein the isolated protected gentamicin $C_{1a}$ is N-ethylated by reaction with acetaldehyde and hydrogenation of the intermediate Schiff base, and the resultant protected 1-N-ethyl gentamicin $C_{1a}$ is deprotected to produce said resultant 1-N-ethyl gentamicin $C_{1a}$.

17. The method of claim 16, wherein said resultant 1-N-ethylgentamicin $C_{1a}$ is extracted from the reaction mixture using an adsorbing resin.

* * * * *

UNITED STATES PATENT AND TRADEMARK OFFICE
CERTIFICATE OF CORRECTION

PATENT NO. : 5,814,488
DATED : September 29, 1998
INVENTOR(S) : Min ZHAO et al.

It is certified that error appears in the above-identified patent and that said Letters Patent is hereby corrected as shown below:

On the title page,
Item [73] Assignee contains a typographical error wherein "Jiansgu Institute of Microbiology, Wuxi China" should read --Jiangsu Institute of Microbiology, Wuxi China--; and Item [57] ABSTRACT, line 8, delete "accitives" and insert --additives--.

Signed and Sealed this

First Day of June, 1999

*Attest:*

Q. TODD DICKINSON

*Attesting Officer*  *Acting Commissioner of Patents and Trademarks*